(12) United States Patent
Duchnowski

(10) Patent No.: US 11,059,060 B2
(45) Date of Patent: *Jul. 13, 2021

(54) TUBULAR HOLDER

(71) Applicant: Michelle Duchnowski, East Meadow, NY (US)

(72) Inventor: Michelle Duchnowski, East Meadow, NY (US)

(*) Notice: Subject to any disclaimer, the term of this patent is extended or adjusted under 35 U.S.C. 154(b) by 354 days.

This patent is subject to a terminal disclaimer.

(21) Appl. No.: 16/055,545

(22) Filed: Aug. 6, 2018

(65) Prior Publication Data

US 2018/0369840 A1 Dec. 27, 2018

Related U.S. Application Data

(63) Continuation of application No. 15/629,210, filed on Jun. 21, 2017, now Pat. No. 10,040,080.

(51) Int. Cl.
*B05B 11/04* (2006.01)
*A61M 35/00* (2006.01)
(Continued)

(52) U.S. Cl.
CPC ............ *B05B 7/1431* (2013.01); *A45D 34/00* (2013.01); *A45D 40/00* (2013.01); *A45D 40/0075* (2013.01); *A61K 9/0014* (2013.01); *B05B 7/241* (2013.01); *B65D 35/00* (2013.01); *A61J 1/067* (2013.01); *A61K 9/06* (2013.01);
(Continued)

(58) Field of Classification Search
CPC ..... B05B 7/1431; B05B 11/047; B05B 7/241; B05B 11/0039; A45D 40/00; A45D 34/00; A45D 40/0075; A61M 2210/04; A61M 35/003; A61J 1/067; B65D 1/095; B65D 35/00; B65D 75/58; B65D 83/00; A61K 9/06; A61K 9/0014
See application file for complete search history.

(56) References Cited

U.S. PATENT DOCUMENTS 1,668,960 A 5/1925 Grimmeisen
1,988,058 A 1/1935 Traller
(Continued)

OTHER PUBLICATIONS

U.S. Notice of Allowance dated Apr. 2, 2018 received in U.S. Appl. No. 15/629,210.
(Continued)

*Primary Examiner* — Adam Marcetich
(74) *Attorney, Agent, or Firm* — Scully, Scott, Murphy & Presser, P.C.

(57) ABSTRACT

The present disclosure is directed to a holder. The holder includes a main body, the main body including an interior surface and an exterior surface, a film that extends around at least a portion of the circumference of a first end of the main body and covers an opening of the first end of the main body, and a sheet including a first surface and a second surface, the second surface opposed to the first surface, the first surface operably attached to the seal at at least one point, the sheet configured to extend a distance along an interior of the main body from the first end towards a second end, wherein at least a portion of the first surface of the sheet contacts the interior surface of the main body, and wherein a liquid composition contacts a second surface of the sheet.

20 Claims, 7 Drawing Sheets

(51) Int. Cl.

| | | |
|---|---|---|
| *A61J 1/06* | (2006.01) | |
| *B65D 1/09* | (2006.01) | |
| *B05B 11/00* | (2006.01) | |
| *B65D 75/58* | (2006.01) | |
| *B65D 83/00* | (2006.01) | |
| *B05B 7/14* | (2006.01) | |
| *B05B 7/24* | (2006.01) | |
| *A61K 9/00* | (2006.01) | |
| *B65D 35/00* | (2006.01) | |
| *A45D 40/00* | (2006.01) | |
| *A45D 34/00* | (2006.01) | |
| *A61K 9/06* | (2006.01) | |

(52) U.S. Cl.
CPC ....... *A61M 35/003* (2013.01); *A61M 2210/04* (2013.01); *B05B 11/0039* (2018.08); *B05B 11/047* (2013.01); *B65D 1/095* (2013.01); *B65D 75/58* (2013.01); *B65D 83/00* (2013.01)

(56) References Cited

U.S. PATENT DOCUMENTS

| | | | | |
|---|---|---|---|---|
| 2,019,552 | A | | 11/1935 | Watts |
| 2,110,615 | A | * | 3/1938 | Wilcox ................ B65D 83/005 206/525 |
| 5,048,727 | A | * | 9/1991 | Vlasich .................. B05B 11/00 222/209 |
| 5,236,120 | A | | 8/1993 | Kleemola |
| 5,567,455 | A | * | 10/1996 | Alsbrook, Sr. ...... A21C 15/007 426/115 |
| 5,632,378 | A | * | 5/1997 | Provost ................. B65D 75/52 206/460 |
| 6,261,611 | B1 | | 7/2001 | Berman |
| 6,478,191 | B1 | | 11/2002 | D'Alessio et al. |
| 6,602,529 | B1 | | 8/2003 | Lonergan et al. |
| 7,077,291 | B1 | | 7/2006 | Bell |
| 10,118,466 | B1 | * | 11/2018 | Horn ....................... A61L 9/035 |
| 2002/0102375 | A1 | * | 8/2002 | Amano ............. B65D 75/5855 428/36.9 |
| 2004/0058038 | A1 | | 3/2004 | Lee |
| 2005/0276653 | A1 | | 12/2005 | L'oreal |
| 2006/0163287 | A1 | * | 7/2006 | Boumnso ........... B65D 83/0055 222/209 |
| 2006/0226171 | A1 | * | 10/2006 | Sternberg ........... B65D 83/0055 222/95 |
| 2007/0119862 | A1 | | 5/2007 | Backes et al. |
| 2008/0017662 | A1 | | 1/2008 | Loranger |
| 2010/0054636 | A1 | | 3/2010 | Owensby et al. |
| 2010/0124591 | A1 | * | 5/2010 | Feldmeier .......... B65D 81/3453 426/120 |
| 2012/0074176 | A1 | | 3/2012 | Sullivan et al. |
| 2012/0312839 | A1 | * | 12/2012 | Stehli, Jr. ................ B65B 3/045 222/184 |
| 2013/0206632 | A1 | * | 8/2013 | Conlon .............. B65D 75/5844 206/499 |
| 2014/0053952 | A1 | | 2/2014 | Genosar |
| 2014/0308408 | A1 | | 10/2014 | Domingues et al. |
| 2014/0339257 | A1 | * | 11/2014 | Ben-Arie ........... B65D 83/0066 222/104 |
| 2017/0081103 | A1 | * | 3/2017 | Tacheny ................ B65D 47/249 |
| 2017/0325577 | A1 | * | 11/2017 | El Eglick ................ B65D 75/42 |
| 2017/0348517 | A1 | * | 12/2017 | Colombo ............. A61M 35/003 |

OTHER PUBLICATIONS

U.S. Office Action dated Aug. 22, 2017 received in U.S. Appl. No. 15/629,210.

* cited by examiner

TUBULAR HOLDER

CROSS REFERENCE TO RELATED APPLICATIONS

The present application is a continuation of a co-pending application having U.S. Ser. No. 15/629,210, filed on Jun. 21, 2017, the entire contents of which are incorporated herein by reference.

BACKGROUND OF THE DISCLOSURE

The transport and use of various liquids and/or solids from a user's home, while travelling, is difficult and cumbersome. For example, purchase of a product in a liquid and/or solid form, for example a diaper cream, is typically purchased in a large tub, tube or a rectangular container that is not convenient for travelling with and using outside the home. Further, it is difficult to reliably store a portion of the cream from the original container to another more portable container for later use.

The use of various liquids and/or solids, for example a diaper cream, while travelling can also lead to leakage of the cream and/or drying out of the cream product, rendering the cream product less useful. Also, applying various liquids and/or solids, for example a diaper cream, while a person or child is at another location, such as in a day care setting, or during a diaper change in a home, can be difficult.

What is desired is a device and method for storing various liquids and/or solids in a holder that can maintain the liquid and/or solid during storage, make application of the liquid and/or solid easy and be disposed of after use. Embodiments of the present disclosure provide methods that address the above and other issues.

SUMMARY OF THE DISCLOSURE

The present disclosure is directed to a holder. The holder includes a main body, the main body including an interior surface and an exterior surface, a film that extends around at least a portion of the circumference of a first end of the main body and covers an opening of the first end of the main body, and a sheet including a first surface and a second surface, the second surface opposed to the first surface, the first surface operably attached to the seal at at least one point, the sheet configured to extend a distance along an interior of the main body from the first end towards a second end, wherein at least a portion of the first surface of the sheet contacts the interior surface of the main body, and wherein a liquid composition contacts a second surface of the sheet.

BRIEF DESCRIPTION OF THE DRAWINGS

The present disclosure will be better understood by reference to the following drawings of which.

DETAILED DESCRIPTION OF THE DISCLOSURE

Figure 1A:
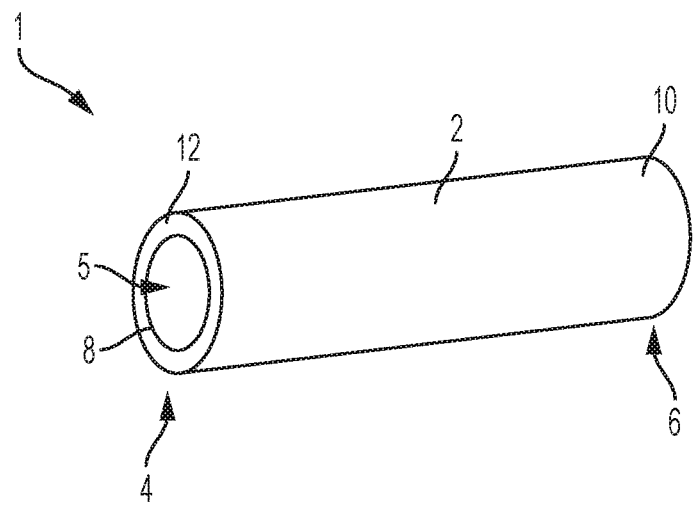
FIG. 1A is a perspective view of a main body.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

In the discussion and claims herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either be completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc.

As used herein the term "tubular" refers to an elongate article having an internal chamber running substantially along the length thereof. While it is expected that the tubular products of the present disclosure can have a substantially circular cross-sectional configuration, it is contemplated that other cross-sectional configurations, such as substantially triangular, substantially rectangular, substantially pentagonal (including other geometric shapes with 6, 7 or more sides) and substantially ellipsoidal, may also be used.

As used herein the term "liquid composition" should be understood to encompass one or more of a liquid, a balm, a solution, an aqueous dispersion, a cream, a lotion, a gel, an emulsion, a water-in-oil emulsion, an oil-in-water emulsion, a paste, an oil, a solvent based liquid, an alcohol based liquid, a pH modifying liquid and so forth.

As used herein, the term "non-woven" material should be understood to encompass any non-woven material or fabric. Non-limiting examples of non-woven material/fabric are materials/fabrics based on cellulose fibers, biopolymers such as, but not limited to flexible packaging materials, plastic based materials, polylactic acid, synthetic polymeric fibers such as, but not limited to polyester, polypropylene and combinations thereof.

As used herein, the term "woven" material refers to a fabric containing a structure of fibers, filaments or yarns, which are orderly arranged in an interengaged fashion, woven fabrics typically contain interengaged fibers in a "warp" and "fill" direction. The warp direction corresponds to the length of the fabric while the fill direction corresponds to the width of the fabric. Woven fabrics can be made on a variety of looms including, but not limited to, shuttle looms, Rapier looms, projectile looms, air jet looms and water jet looms.

The tubular holder 1 of the present disclosure is illustrated in FIG. 1. The tubular holder 1 includes a tubular main body 2. Tubular main body 2 can be composed of any suitable material, such as but not limited to paper based materials, including cardboard, plastics, metals, ceramic based materials, including glass, carbon based materials, including carbon fibers, and mixtures thereof.

The tubular main body 2 includes a first end 4 and a second end 6, and includes an interior surface 8 and an exterior surface 10. Around the circumference of the first end 4 is a lip 12, which is the transition between the interior surface 8 and the exterior surface 10. An opening 5 extends through the tubular main body 2 from the first end 4 to the second end 6.

The tubular main body 2 can be substantially rigid, or substantially deformable in any direction, with the deformability or the rigidity being adjustable as desired.

Figure 1B:
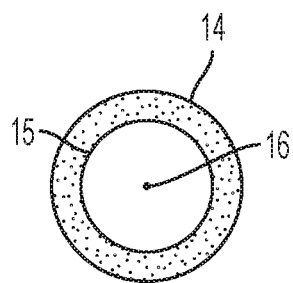
FIG. 1B is a plan view of a film.

In FIG. 1B a film 14 is shown. The film 14 is configured to extend around at least a portion of the circumference of the first end 4 of the tubular main body 2 and also cover the opening 5. The film 14 is shown as substantially circular in FIG. 1B, but, in other embodiments film 14 can be any suitable shape that can extend around at least a portion of the circumference of the first end 4 of the tubular main body 2.

The film 14 can be formed of any suitable woven and/or non-woven material that can maintain a sheet (discussed below) in relation to the tubular main body 2. The sheet is operably attached to the film 14 at at least film point 16. Although film point 16 is shown in substantially the center of film 14, the film point 16 can be in any suitable location.

The film 14 can also include an adhesive 15 that is configured to maintain the film 14 in contact with the first end 4. Alternatively or additionally, an adhesive can be included in the vicinity of the lip 12 on the exterior surface 10 of the tubular main body 2.

Figure 1C:
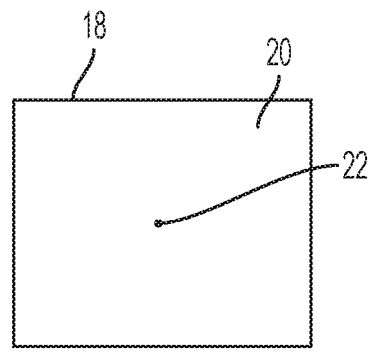
FIG. 1C is a plan view of a sheet.

In FIG. 1C a sheet 18 is shown, with the sheet 18's first surface 20 visible in FIG. 1C. In the figures, sheet 18 is shown as being substantially rectangular for illustrative purposes, but in other embodiments, sheet 18 can be any suitable shape, such as substantially circular, substantially elliptical, substantially triangular, a shape with an erratic outline, or a shape with five or more sides.

Sheet 18 also includes a second surface opposed to the first surface, which is shown in further figures below. On the first surface 20 a sheet point 22 is included, which is configured to be operably attached to the film point 16 in any suitable way, such as by an adhesive or by a mechanical connection such as a staple, sewing through both the sheet 18 and the film 14, or the like. Although sheet point 22 is shown in substantially the center of the sheet 18, the sheet point 22 can be in any suitable location. Also, the point 22 can be larger than a single point, and can cover an area that is about 50% of the area of the opening 5 or about an area that is about 100% of the area of the opening 5.

Figure 1D:
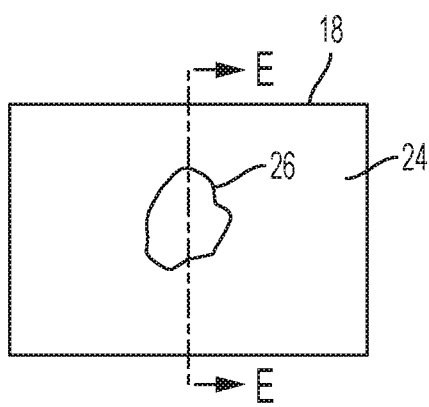
FIG. 1D is a plan view of a sheet.

The opposing surface, second surface 24, of sheet 18 is shown in FIG. 1D. Contacting the second surface 24 is a liquid composition 26. Although the liquid composition 26 is shown as being in substantially the center of the second surface 24, the liquid composition 26 can be in any one or more suitable locations. The sheet 18 can be formed of any suitable woven and/or non-woven material that can maintain the liquid composition 26 in relation to the tubular main body 2. The liquid composition 26 can maintain its position on sheet 18 due to any cohesive and/or adhesive force.

Figure 1E:
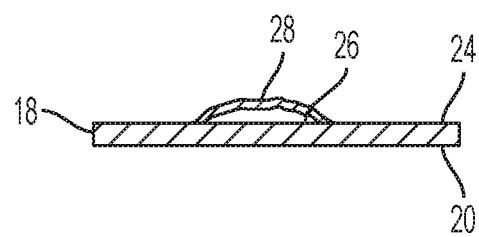
FIG. 1E is a side view of a sheet.

A side cross-sectional view of FIG. 1D is shown in FIG. 1E. In FIG. 1E both the first surface 20 and the second surface 24 can be seen. The liquid composition 26 is shown as contacting the second surface 24, in an embodiment where the sheet is substantially non-absorbent, but, in other embodiments the liquid composition 26 can penetrate a distance into sheet 18 through the second surface 24 towards the first surface 20. Also shown is an optional liquid covering 28 covering at least a portion of the liquid composition 26. Liquid covering 28 can be any substantially impermeable material that can be broken open manually by a user of the tubular holder 1 to allow for egress of the liquid composition 26. The liquid covering 28 can also surround the liquid composition 26, contacting the second surface 24 around a periphery of the liquid composition 26.

Figure 2:
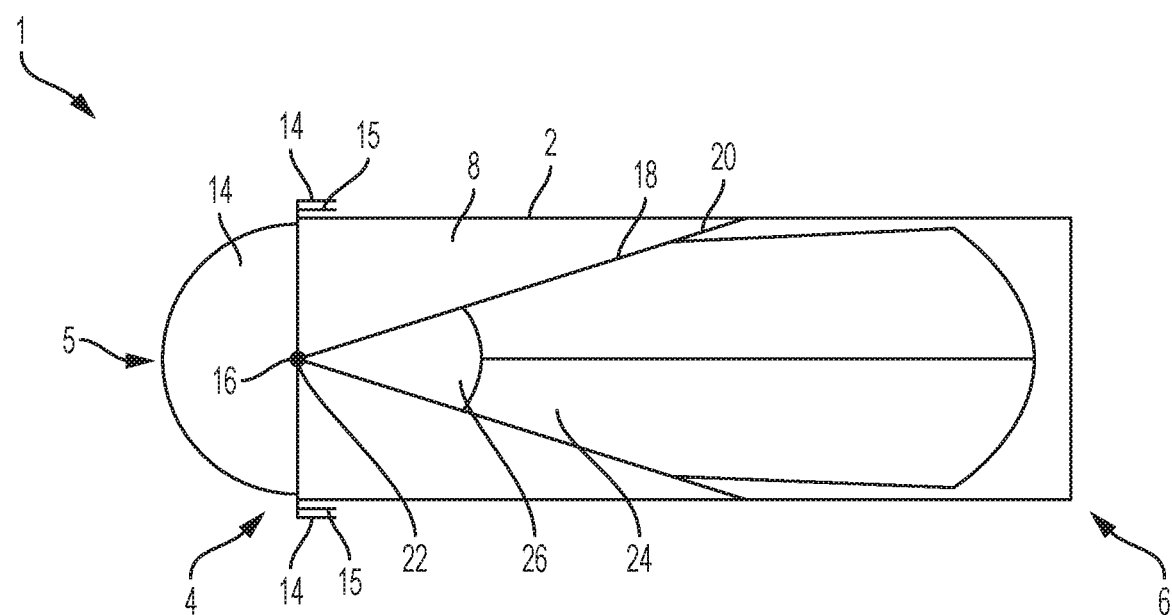
FIG. 2 is a cross-sectional side view of a holder.

FIG. 2 is a cross sectional view of tubular holder 1, with each of the components of FIGS. 1A-1E shown together.

In this embodiment, the film 14 is extending around a portion of the circumference of the first end 4, covering the opening 5. The adhesive 15 is included in this embodiment, around the circumference of the first end 4, adhering the film 14 to the exterior surface 10 of the tubular main body 2. In other embodiments the adhesive 15 can adhere the film 14 to just the lip 12, or, the adhesive 15 can adhere the film 14 to both the lip 12 and around the circumference of the exterior surface 10 of the first end 4. Although not shown in this figure, a second film can optionally extend around the second end 6 of the tubular main body 2. In other embodiments, the material of the tubular main body 2 can extend across the second end 6 as a separate element, or as an extension of the exterior surface 10, to cover or substantially cover an opening of the second end 6.

The film point 16 is operably attached to the sheet 18 at the sheet point 22. As can be seen the sheet point 22 is operably attached to the film point 16.

The sheet 18 is shown as extending a distance along an interior of the tubular main body 2 from the first end 4 to the second end 6. In this embodiment a portion of the first surface 20 of the sheet 18 contacts the interior surface 8 of the tubular main body 2. The diameter and circumference of tubular main body 2 can be configured to substantially maintain the sheet 18 in the position of FIG. 2. For example, for a larger surface area sheet 18, a larger diameter tubular main body 2 can be used. As one non-limiting example of the dimensions of these features, a sheet of about four inches in diameter can be used with a tubular main body having about a two inch length and about a ¾ inch diameter. Included in this example the sheet can include a premeasured amount of a liquid composition depending on application needs.

The sheet 18 can be folded or compressed in any suitable way so that it can fit within the tubular main body 2.

Contained by the second surface 24 of the sheet 18, the liquid composition 26 remains substantially stationary within the tubular main body 2 and is substantially maintained in the position of FIG. 2.

The above examples illustrate just a few of the many sizes and shapes each of the components of the tubular holder 1 can be. Other examples can include other shapes and sizes that are capable of performing the same or a similar function.

The methods and devices of the present disclosure will be better understood by reference to the following Examples, which are provided as exemplary of the disclosure and not by way of limitation.

Example 1

Figure 3A:
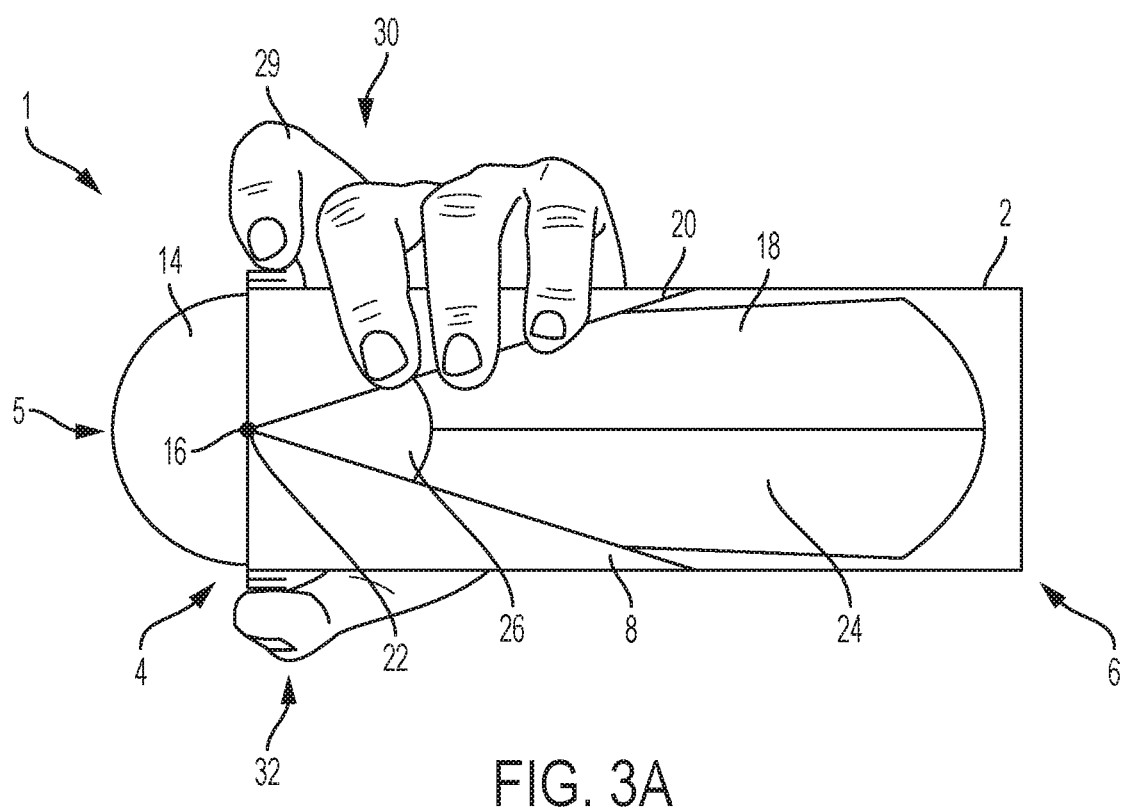
FIG. 3A is a cross-sectional side view of a holder and a user's hand.

In the present example, a user operates the tubular holder 1 so that liquid composition 26 can be accessed. In FIG. 3A, a user moves their hand 29 so that it is in contact with the tubular main body 2 near the first end 4. In this example, tubular main body 2 is substantially rigid.

The user then exerts a pressure in substantially the direction of arrows 30 and 32 to substantially maintain the position of the first end 4 of the tubular main body 2. In this embodiment the pressure to the main body is exerted by the user's hand 29, but in other embodiments, any device or implement can be used to apply pressure to the first end 4.

Figure 3B:
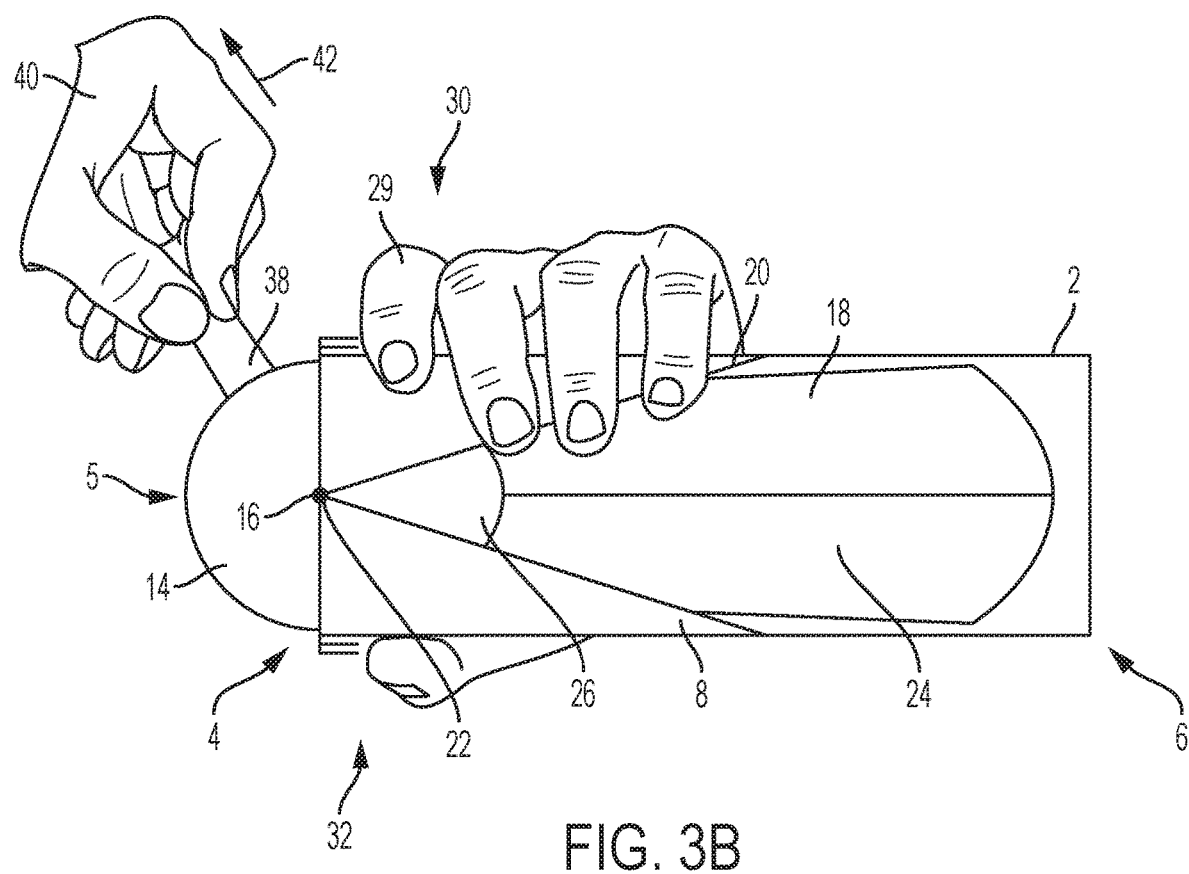
FIG. 3B is a cross-sectional side view of a holder, in a non-deformed configuration, and a user's hand.

Once pressure is applied, the tubular main body 2 is in the configuration shown in FIG. 3B. With the user's other hand 40 (or another suitable device or implement) a tab 38 is grasped and pulled in substantially the direction of arrow 42. Tab 38 is operably connected to the film 14 as a continuous element of the film 14 or a separate piece of material. Tab 38 can be of any suitable shape and size that allows for the tab 38 to be grasped and pulled to remove the film 14 from the tubular main body 2.

Figure 3C:
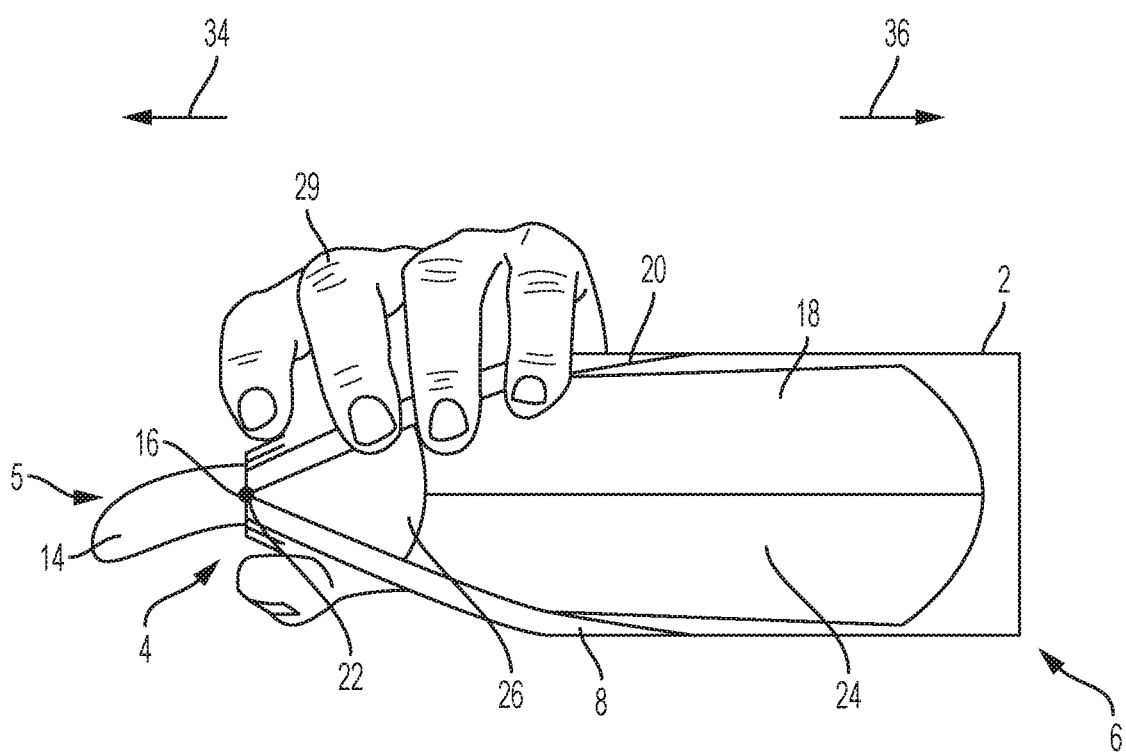
FIG. 3C is a cross-sectional side view of a holder, in a deformed configuration, and a user's hand.
Figure 3D:
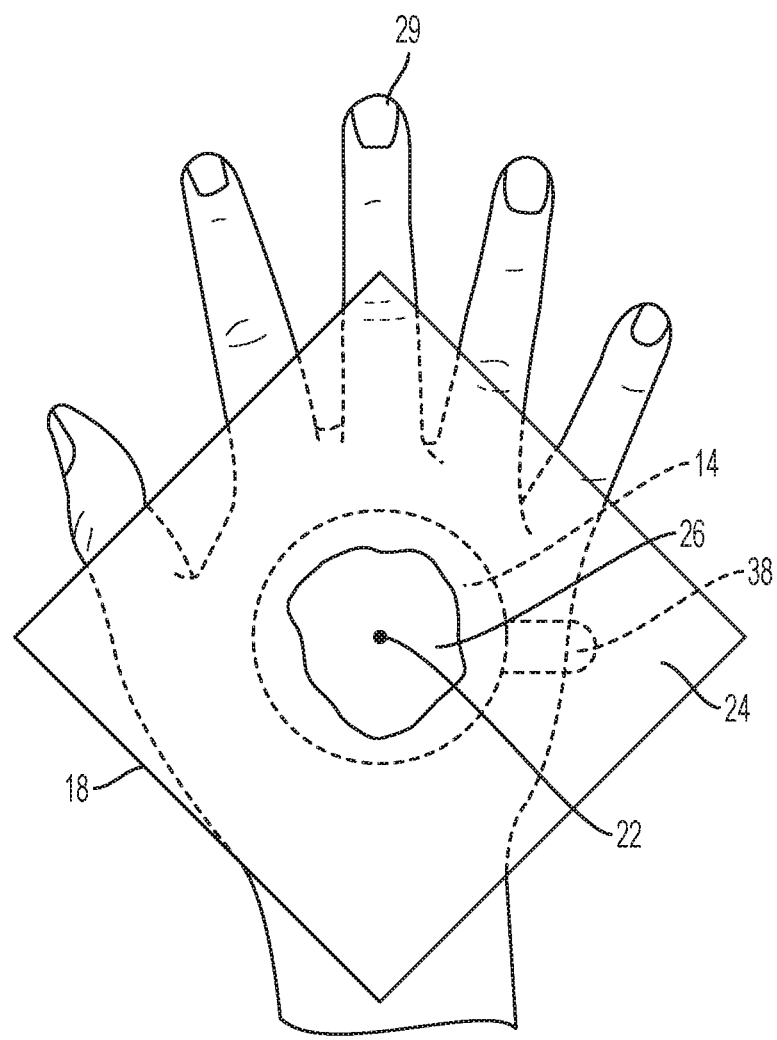
FIG. 3D is a plan view of a sheet and a user's hand.

Once the tab 38 and film 14 are removed from the tubular main body 2, the second surface 24 and liquid composition 26 can be exposed, as shown in FIG. 3D.

In FIG. 3D the user can hold the film 14 and sheet 18, with the first surface 20 contacting the user's hand 29. The second surface 24, along with the liquid composition 26 is then exposed and ready for use by the user. In this embodiment the liquid composition 26 is applied to a portion of the user, or another person—such as a child—or any other suitable surface and then all components of the tubular holder 1 are disposed of after the single use.

Example 2

In the present example, a user operates the tubular holder 1 so that liquid composition 26 can be accessed. In FIG. 3A, a user moves their hand 29 so that it is in contact with the tubular main body 2 near the first end 4. The user may also contact the film 14 with their hand 29. In this embodiment, tubular main body 2 is substantially deformable.

In this example, the user exerts a pressure (from what is shown in FIG. 3A) in substantially the direction of arrows 30 and 32 to deform the first end 4 of the tubular main body 2, as shown in FIG. 3C. In this embodiment the pressure to deform the first end 4 of the main body is exerted by the user's hand 29, but in other embodiments, any device or implement can be used to deform the first end 4. The resulting, deformed tubular main body 2 is shown in FIG. 3C.

Once the tubular main body 2 is in the configuration shown in FIG. 3C, a force is exerted between the film 14 and the tubular main body 2 in substantially the direction of arrow 34 and/or arrow 36. Combined with the deformation force illustrated in FIG. 3A, the force exerted in substantially the direction of arrow 34 and/or arrow 36 causes the adhesive 15 that attaches the film 14 to the tubular main body 2 to detach so that the second surface 24 and liquid composition 26 can be exposed, as shown in FIG. 3E.

Figure 3E:
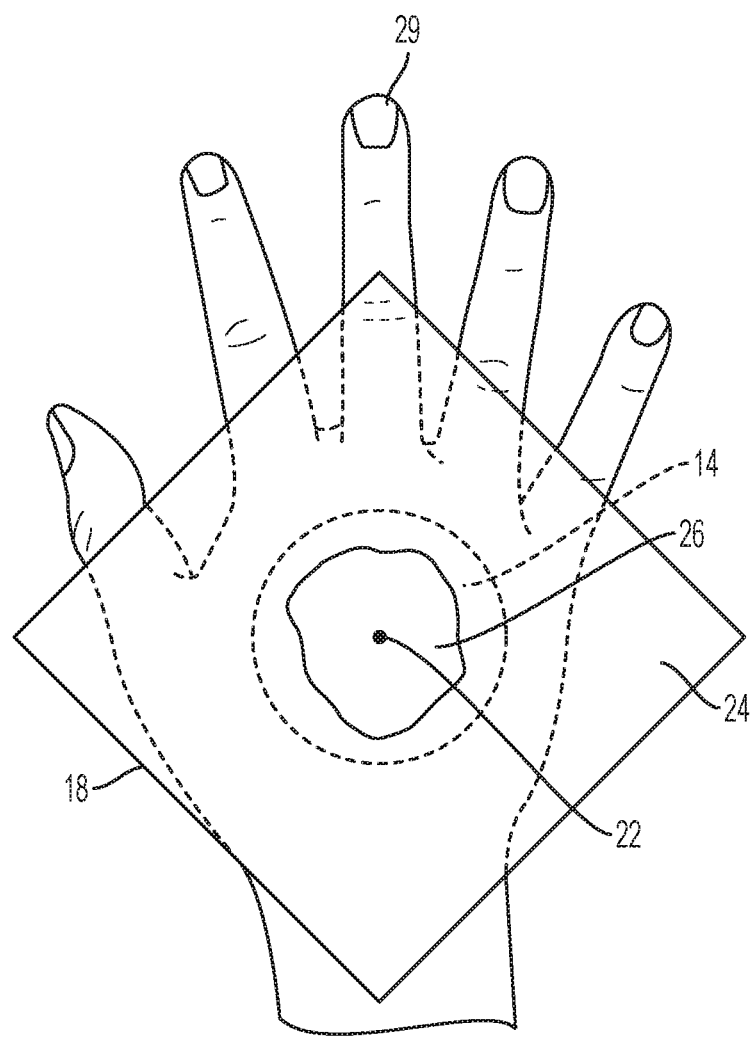
FIG. 3E is a plan view of a sheet and a user's hand.

In FIG. 3E the user can hold the film 14 and sheet 18, with the first surface 20 contacting the user's hand 29. The second surface 24, along with the liquid composition 26 is then exposed and ready for use by the user. In this embodiment the liquid composition 26 is applied to a portion of the user, or another person—such as a child—or any other suitable surface and then all components of the tubular holder 1 are disposed of after the single use.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A holder, the holder comprising:
 a main body, the main body comprising an interior surface and an exterior surface;

a film that extends around at least a portion of the circumference of a first end of the main body and covers an opening of the first end of the main body;

a sheet comprising a first surface and a second surface, the second surface opposed to the first surface, the first surface operably attached to a seal at one or more points, the sheet configured to extend along an interior of the main body from the first end towards a second end, wherein at least a portion of the first surface of the sheet contacts the interior surface of the main body, and wherein a liquid composition contacts a second surface of the sheet, wherein a first void is present between the second surface of the sheet and the second end of the main body, and wherein the first void is a majority of a volume between the second surface of the sheet and the second end of the main body.

2. The holder of claim 1, wherein the sheet is formed of a woven material, a non-woven-material, and combinations thereof.

3. The holder of claim 1, wherein the sheet is configured to maintain the liquid composition within the main body.

4. The holder of claim 1, wherein a liquid covering covers at least a portion of the liquid composition.

5. The holder of claim 4, wherein the liquid covering surrounds the liquid composition and contacts the second surface of the sheet around a periphery of the liquid composition.

6. The holder of claim 1, wherein the film is adhered to the exterior surface of the main body around the circumference of the first end.

7. The holder of claim 1, wherein a transition between the interior surface of the main body and the exterior surface of the main body forms a lip at the first end, and wherein the film is adhered to the lip.

8. The holder of claim 7, wherein the film is also adhered to the exterior surface of the main body around the circumference of the first end.

9. The holder of claim 1, wherein the main body is substantially rigid.

10. The holder of claim 1, wherein the main body is substantially deformable.

11. The holder of claim 1, wherein the film further comprises a tab extending from the film.

12. A method of applying a liquid composition comprising:

removing a film from a main body, the main body comprising an interior surface and an exterior surface; the film extends around at least a portion of the circumference of a first end of the main body and covers an opening of the first end of the main body;

a sheet comprising a first surface and a second surface, the second surface opposed to the first surface, the first surface operably attached to a seal at one or more points, the sheet configured to extend a distance along an interior of the main body from the first end towards a second end, wherein at least a portion of the first surface of the sheet contacts the interior surface of the main body, and wherein a liquid composition contacts a second surface of the sheet, wherein a first void is present between the second surface of the sheet and the second end of the main body, and wherein the first void is a majority of a volume between the second surface of the sheet and the second end of the main body;

exposing the liquid composition from the sheet; and applying the liquid composition to a surface.

13. The method of claim 12, wherein the surface is a surface of a human's skin.

14. The method of claim 12, wherein the film is removed by the pulling of a tab operably connected to the film.

15. The holder of claim 1, further comprising a second film that extends around at least a portion of the circumference of the second end of the main body and covers an opening of the second end of the main body.

16. The holder of claim 1, wherein the liquid composition is selected from the group consisting of a balm, a cream, a lotion, a gel and a paste.

17. The holder of claim 1, wherein the sheet is operably attached to the film at only a point that is substantially the center of the film.

18. The holder of claim 1, wherein a second void is present between the first surface of the sheet and the film.

19. The method of claim 12, wherein the main body further comprises a second film that extends around at least a portion of the circumference of the second end of the main body and covers an opening of the second end of the main body.

20. The method of claim 12, wherein a second void is present between the first surface of the sheet and the film.

* * * * *